US009060959B2

(12) United States Patent
Shapira et al.

(10) Patent No.: US 9,060,959 B2
(45) Date of Patent: Jun. 23, 2015

(54) SYNERGISTIC COMPOSITIONS AND METHOD FOR POTENTIATING ANTI-OXIDATIVE ACTIVITY

(75) Inventors: Niva Shapira, Tel-Aviv (IL); Joseph Kanner, Rechovot (IL)

(73) Assignee: The State of Israel, Ministry of Agriculture & Rural Development, Agricultural Research Organization (ARO) (Volcani Center), Beit-Dagan (IL)

(*) Notice: Subject to any disclaimer, the term of this patent is extended or adjusted under 35 U.S.C. 154(b) by 1369 days.

(21) Appl. No.: 10/543,022

(22) PCT Filed: Jan. 25, 2004

(86) PCT No.: PCT/IL2004/000071
§ 371 (c)(1),
(2), (4) Date: Sep. 14, 2006

(87) PCT Pub. No.: WO2004/064719
PCT Pub. Date: Aug. 5, 2004

(65) Prior Publication Data
US 2007/0014876 A1 Jan. 18, 2007

Related U.S. Application Data

(60) Provisional application No. 60/442,049, filed on Jan. 24, 2003.

(51) Int. Cl.
*A61K 9/00* (2006.01)
*A61K 33/06* (2006.01)
*A61K 9/48* (2006.01)
*A61K 9/14* (2006.01)
*A61K 45/06* (2006.01)
*A61K 47/00* (2006.01)
*A61K 9/68* (2006.01)
*A61K 31/00* (2006.01)
*A61K 31/05* (2006.01)
*A61K 33/08* (2006.01)
*A61K 33/10* (2006.01)

(52) U.S. Cl.
CPC ............... *A61K 31/00* (2013.01); *A61K 31/05* (2013.01); *A61K 33/06* (2013.01); *A61K 33/08* (2013.01); *A61K 33/10* (2013.01); *A61K 45/06* (2013.01)

(58) Field of Classification Search
CPC ... A61K 2300/00; A61K 31/00; A61K 33/06; A61K 31/05; A61K 33/08; A61K 33/10; A61K 45/06
USPC ............... 424/682; 514/255.05, 27, 338, 400, 514/456, 464, 469, 533, 731
See application file for complete search history.

(56) References Cited

U.S. PATENT DOCUMENTS

| 4,327,076 | A | | 4/1982 | Puglia et al. | |
|---|---|---|---|---|---|
| 4,806,354 | A | | 2/1989 | Green | |
| 4,824,672 | A | * | 4/1989 | Day et al. | 424/738 |
| 4,913,909 | A | * | 4/1990 | Hara et al. | 424/688 |
| 5,380,530 | A | * | 1/1995 | Hill | 424/440 |
| 5,667,802 | A | * | 9/1997 | Grimberg | 424/464 |
| 5,708,017 | A | * | 1/1998 | Dave et al. | 514/393 |
| 5,935,600 | A | | 8/1999 | Cherukuri et al. | |
| 6,025,387 | A | | 2/2000 | Yoo et al. | |
| 6,040,333 | A | * | 3/2000 | Jackson | 514/456 |
| 6,099,854 | A | * | 8/2000 | Howard et al. | 424/440 |
| 6,284,265 | B1 | * | 9/2001 | Lambert et al. | 424/439 |
| 6,288,081 | B1 | | 9/2001 | Petersen et al. | |
| 6,294,586 | B1 | | 9/2001 | Yelle et al. | |
| 6,299,925 | B1 | * | 10/2001 | Xiong et al. | 426/597 |
| 6,372,264 | B1 | * | 4/2002 | Dixon | 424/677 |
| 6,413,546 | B1 | * | 7/2002 | He et al. | 424/464 |
| 2007/0014876 | A1 | | 1/2007 | Shapira et al. | |

FOREIGN PATENT DOCUMENTS

| WO | WO02/051259 A1 * | 7/2002 | 424/401 |
|---|---|---|---|
| WO | WO 2004/064719 | 8/2004 | |

OTHER PUBLICATIONS

Handelman, Garry J., et al. "Antioxidant Capacity of Oat (*Avena sativa* L.) Extracts, 1. Inhibition of Low-Density Lipoprotein Oxidation and Oxygen Radical Absorbance Capacity." J. Agric. Food Chem. 1999, 47, 4888-4893.*
Ahn et al. "Efficacy of Use of Colonoscopy in Dextran Sulfate Sodium Induced Ulcerative Colitis in Rats: The Evaluation of the Effects of Antioxidant by Colonoscopy", International Journal of Colorectal Diseases, 16(3): 174-181, 2001. Abstract.
Cheong et al. "[Suppressive Effects of Antioxidants DA-9601 on Hepatic Fibrosis in Rats"], Taehan Kan Hakhoe Chi, 8(4): 436-447, 2002. Abstract. Article in Korean.
Fitzgerald "Beyond Acid Suppressants in Gastro-Oesophageal Reflux Disease", Gut, 49: 319-321, 2001.
Hahm et al. "Induction of Apoptosis With an Extract of *Artemisia asiatica* Attenuates the Severity of Cerulein-Induced Pancreatitis in Rats", Pancreas, 17(2): 153-157, 1998. Abstract.
Huh et al. "Inhibitory Effects of DA-9601 on Ethanol-Induced Gastrohemorrhagic Lesions and Gastric Xanthine Oxidase Activity in Rats", Journal of Ethnopharmacology, 88(2-3): 269-273, 2003. Abstract.

(Continued)

*Primary Examiner* — Andrea Buckley (57) ABSTRACT

The present invention relates to synergistic compositions for protection against oxidative damage, consisting essentially of antacids in conjunction with antioxidants. The invention further relates to method for preventing oxidative damage using the compositions of the invention.

14 Claims, 2 Drawing Sheets

(56) References Cited

OTHER PUBLICATIONS

Ji et al. "Metabolism of Eupatilin in Rats Using Liquid Chromatography/Electrospray Mass Spectometry", Biomedical Chromatography, 18(3): 173-177, 2004. Abstract.
Kim et al. "Combined Use of Omeprazole and a Novel Antioxidative Cytoprotectant for the Treatment of Peptic Ulcer. Facilitation of Ulcer Healing in Experimental Animals", Arzneimittelforschung, 55(7): 387-393, 2005. Abstract.
Lee et al. "Involvement of Oxidative Stress in Experimentally Induced Reflux Esophagitis and Barrett's Esophagus: Clue for the Chemoprevention of Esophageal Carcinoma by Antioxidants", Mutation Research, 480-481: 189-200, 2001. Abstract.
Oh et al. "Oxidative Damages are Critical in Pathogenesis of Reflux Esophagitis: Implication of Antioxidants in Its Treatment", Free Radic. Biol. Med., 30(8): 905-915, 2001. Abstract.
Oh et al. "Oxidative Stress is More Important Than Acid in the Pathogenesis of Reflux Oesophagitis in Rats", Gut, 49(3): 364-371, 2001. Abstract.
Ryu et al. "Studies on Protective Effect of DA-9601, Artemisia Asiatica Extract, on Acetaminophen- and CC14-Induced Liver Damage in Rats", Arch. Pharmacological Research, 21(5): 508-513, 1998. Abstract.
Seo et al. "Inhibitory Effects of the Standardized Extract (DA-9601) of *Artemisia asiatica* Nakai on Phorbol Ester-Induced Ornithine Decarboxylase Activity, Papilloma Formation, Cyclooxygenase-2 Expression, Inducible Nitric Oxide Synthase Expression and Nuclear Transcription Factor Kappa B Activation in Mouse Skin", International Journal of Cancer, 100(4): 456-462, 2002. Abstract.
Seol et al. "DA-9601 for Erosive Gastritis: Results of a Double-Blind Placebo-Controlled Phase III Clinicical Trial", World Journal of Gastroenterology, 10(16): 2379-2382, 2004.
Son et al. "Protective Effect of Taurine on Indomethacin-Induced Gastric Mucosal Injury", Adv. Exp. Med. Biology, 403: 147-155, 1996. Abstract.
Son et al. "Protective Effect of Taurine on TNBS-Induced Inflammatory Bowel Disease in Rats", Arch. Pharmacological Research, 21(5): 531-536, 1998. Abstract.
Son et al. "Taurine Can Ameliorate Inflammatory Bowel Disease in Rats", Adv. Exp. Med. Biology, 442: 291-298, 1998. Abstract.
Yoo et al. "Novel Antioxidant Ameliorates the Fibrosis and Inflammation of Cerulein-Induced Chronic Pancreatitis in a Mouse Model", Pancreatology, 5(2-3): 165-176, 2005. Abstract.
Kanner et al., *The Stomach as a Bioreactor: Dietary Lipid Peroxidation in the Gastric Fluid and the Effects of Plant-Derived Antioxidants*, Free Radical Biology & Medicine (2001), vol. 31, No. 11, pp. 1385-1395.
International Preliminary Report on Patentability Dated Jul. 29, 2005 From the International Bureau of WIPO Re.: Application No. PCT/IL2004/000071.
Office Action Dated Aug. 12, 2008 From the Israeli Patent Office Re.: Application No. 169793.
Examiner's Report Dated Aug. 4, 2008 From the Australian Government, IP Australia Re.: Application No. 2004206141.
International Search Report Dated Apr. 1, 2005 From the International Searching Authority Re.: Application No. PCT/IL04/00071.
Response Dated Nov. 23, 2009 to Official Action of Oct. 23, 2009 From the US Patent and Trademark Office Re.: U.S. Appl. No. 10/543,022.
Written Opinion Dated Apr. 1, 2005 From the International Searching Authority Re.: Application No. PCT/IL04/00071.
Translation of Office Action Including Asamura's Comments Dated Mar. 2, 2010 From the Japanese Patent Office Re.: Application No. 2006-500382.
Office Action Dated Apr. 1, 2012 From the Israeli Patent Office Re.: Application No. 169793 and Its Translation Into English.
Response Dated Jul. 12, 2011 to Office Action of Aug. 12, 2008 From the Israeli Patent Office Re.: Application No. 169793.
Fitzgerald "Beyond Acid Suppressants in Gastro-Oesophageal Reflux Disease", Gut, 49: 320-321, Sep. 2001.
Kanner et al. "The Stomach as a Bioreactor: Dietary Lipid Peroxidation in the Gastric Fluid and the Effect of Plant-Derived Antioxidants", Free Radical Biology & Medicine, 31(11): 1385-1395, 2001. Abstract.
Office Action Dated Feb. 19, 2014 From the Israeli Patent Office Re. Application No. 169793 and Its Translation Into English.

\* cited by examiner

SYNERGISTIC COMPOSITIONS AND METHOD FOR POTENTIATING ANTI-OXIDATIVE ACTIVITY

CROSS REFERENCE TO RELATED APPLICATIONS

This application is a 35 U.S.C. §371U.S. national stage filing from PCT Application Ser. No. PCT/IL2004/000071 having international filing date of Jan. 25, 2004, which claims priority from U.S. provisional application Ser. No. 60/442,049, filed Jan. 24, 2003, which are hereby incorporated by reference in their entirety.

FIELD OF THE INVENTION

The present invention relates to compositions for protection against oxidative damage and for reducing generation of free radicals and peroxides, consisting essentially of antacids in conjunction with antioxidants. The invention further relates to method for preventing oxidative damage using the compositions of the invention.

BACKGROUND OF THE INVENTION

Gastric acidity is necessary for food digestion and protection against pathogenic bacteria, however, over acidity is also known as a risk factor for stomach ulceration and stomach and esophagus cancer. Free radicals are associated with induction of gastric mucosal injury and stomach ulceration.

A recent publication by one of the inventors of the present invention disclosed that the formation of radicals through lipid peroxidation is inhibited by polyphenols in a dose-dependent manner and that polyphenols stimulate the breakdown of hydroperoxides (Kanner et al., Free Radic. Biol. 31:1388, 2001).

Various classes of drugs are useful for preventing excess acidity in the stomach, and elevating gastric pH, including classical antacids comprising buffering agents, proton pump inhibitors and histamine antagonists.

U.S. Pat. No. 6,294,586 discloses methods and compositions utilizing hydroxyomeprazole for the treatment of ulcers in humans. Hydroxyomeprazole is also useful for the treatment of gastroesophageal reflux and other conditions related to gastric hyper secretion such as Zollinger-Ellison Syndrome.

U.S. Pat. No. 6,288,081 discloses the use of quinolone- and naphthyridonecarboxylic acid derivatives which are substituted in position 7 by a 1-aminomethyl-2-oxa-7-azabicyclo[3.3.0]oct-7-yl radical, for the therapy of *Helicobacter pylori* infections and associated gastro duodenal disorders.

U.S. Pat. No. 6,284,265 discloses an antacid formulation comprising antacid, antioxidant, oil and a selected nutritional acceptable carrier. The antioxidant functions to prevent oxidation and breakdown of the certain components, most likely the oil, prior to consumption.

U.S. Pat. No. 4,806,354 discloses an improved health food composition comprising B complex vitamins, prostaglandin E-1 precursor, analgesic, antacid and optionally a preservative sodium benzoate. Compositions comprising the latter ingredient may further comprise a primary emulsifying agent and a flavoring agent in the absence or in the presence of a secondary emulsifying agent and an antioxidant.

U.S. Pat. No. 4,327,076 discloses a compressed chewable antacid tablet comprising (a) fat composition comprising edible fat material and antioxidants; (b) a mixture of active ingredients comprising an antacid; and (c) direct compaction tabletting aids. The fat composition component is the essential ingredient of the compressed chewable antacid tablet as its presence masks chalkiness, grittiness, dryness and astringent properties of the tablet.

Small amounts of antioxidants are added almost invariably to pharmaceutical and other compositions for protecting the active ingredients during storage. They are also added commonly to preserved foods to prolong shelf life. In small quantities, antioxidants act to prevent oxidation of the active ingredients and to increase shelf life of these compositions as well as of preserved foods, while not intended to alter or improve the efficiency of the active ingredients.

There is an unmet need to provide means for potentiating antioxidative activities thereby reducing or preventing production of peroxides and other free radicals and attenuating or eliminating oxidative damage.

SUMMARY OF THE INVENTION

The present invention relates to compositions containing antioxidants as one of two classes of active ingredient therein and antacids as the second class of active ingredient, wherein the antioxidant and antacid of the compositions of the invention act synergistically.

The present invention provides compositions and methods using same for providing protection from oxidative damage, such as the damage caused by free radicals and peroxides. The present invention further provides compositions and methods using same for protecting epithelial cells in the stomach and the esophagus from oxidative damage, such as the damage caused by peroxides and free radicals. The compositions of the present invention consist essentially of antacids in conjunction with antioxidants and a pharmaceutically acceptable carrier, stabilizer or diluent.

The term "antacid" as used herein is to be construed in its most general sense and refers to materials capable of inhibiting acid production in the stomach or attenuating gastric acidity. These materials encompass broadly the following major categories: classical antacids (e.g. magnesium hydroxide and aluminum carbonate), $H_2$-receptor antagonists or $H_2$ antagonists (e.g. cimetidine, ranitidine, famotidine and nizatidine) and proton pump inhibitors (e.g. omeprazole, hydroxyomeprazole, lansoprazole, esomeprazole, pantoprazole and rabeprazole sodium).

The present invention is based in part on the unexpected discovery that a formulation consisting essentially of an antacid and an antioxidant exhibits increased antioxidative activity as compared with the antioxidative activity of a similar formulation devoid of the antacid component. The enhancement of anti-oxidative activity is generally at least two-fold the activity of a similar formulation devoid of the antacid component, preferably higher.

The inventors have now surprisingly found that introduction of a formulation consisting essentially of an antacid in conjunction with an antioxidant to a gastric system in the presence of pro-oxidative catalysts, converts the activity of these catalysts from pro-oxidative to antioxidative. Without wishing to be bound by any particular theory or mechanism of action this conversion may be attributed to the increase in the pH of the system that is induced by the antacid.

The compositions of the present invention are advantageous over formulations of an antacid alone, as the protective and antioxidative activities of the present compositions are more effective. Thus, the compositions of the present invention may be administered less frequently and/or at lower doses than other antacids known in the art. The composition of the invention may consist of a lower total amount of antacid and hence using the composition of the invention diminishes the damaging side effects associated with relatively high levels of antacids.

According to one embodiment, the surprising antioxidative activity conferred in situ by the formulation of the present invention makes these formulations particularly suitable for preventing or attenuating the formation of gastric mucosal lesions that are generated or exacerbated by peroxides and other free radicals during acid secretion and/or digestion.

As disclosed herein for the first time the strong and effective antioxidative activity of the compositions of the present invention is a synergistic activity per se. Neither of the active ingredients of the formulation, namely the antacid or the antioxidant, exerts such an efficient antioxidative activity when administered alone, in a formulation consisting exclusively or predominantly of this active ingredient.

According to one aspect, the present invention provides a composition for potentiating antioxidative activities, consisting essentially of:
 (a) at least one antacid component in a dose sufficient to elevate the pH in the stomach;
 (b) at least one antioxidant component in a dose sufficient to decrease free radical generation in the stomach; and, optionally,
 (c) at least one pharmaceutically acceptable carrier.

According to the present disclosure the antacid will be present in a dose sufficient to elevate the gastric pH by at least one pH unit, preferably the elevation will be greater than one pH unit.

The terms "sufficient" or "sufficient dose" are interchangeable as used herein to describe an amount that is therapeutically effective for exerting any one of its desired activities in vivo.

According to one embodiment, the compositions have the ability to decrease at least two fold the concentration of free radicals and peroxides in the stomach or esophagus as compared with the ability of a composition comprising the same dose of antioxidant in the absence of antacid.

According to one embodiment, the compositions of the invention may further comprise at least one of the following ingredients: filler, disintegrant, anticaking agent, film coating, binder, sweetening agent, glidant, flavor, color, lubricant, and stabilizers for solution or for solid forms, as are well known in the art of pharmaceuticals.

According to another aspect the synergistic anti-oxidative effects of the compositions of the present invention may be beneficially utilized to prevent oxidation of a pharmaceutically active ingredient during the passage of the pharmaceutically active ingredient through the stomach or GI tract.

According to one embodiment, the present invention provides a pharmaceutical composition, for preventing oxidation of an active pharmaceutical ingredient in the stomach consisting essentially of:
 (a) at least one pharmaceutically active ingredient;
 (b) at least one antacid component in a dose sufficient to elevate the pH in the stomach;
 (c) at least one antioxidant component in a dose sufficient to decrease free radical generation in the stomach; and
 (d) at least one pharmaceutically acceptable carrier, diluent or stabilizer.

According to one embodiment, the antacid component comprises at least one classical antacid selected from the group consisting of: aluminum carbonate, aluminum hydroxide, aluminum phosphate, aluminum hydroxy carbonate, dihydroxy aluminum sodium carbonate, aluminum magnesium glycinate, dihydroxy aluminum aminoacetate, dihydroxyaluminum aminoacetic acid, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

According to yet another embodiment, the antacid component comprises at least one $H_2$-receptor antagonists selected from the group consisting of: cimetidine, ranitidine, famotidine and nizatidine.

According to yet another embodiment, the antacid component comprises at least one proton pump inhibitor selected from the group consisting of: omeprazole, hydroxyomeprazole, lansoprazole, esomeprazole, pantoprazole and rabeprazole sodium.

Some antacids may act by more than one mechanism such as the salts of bismuth that may act both as buffers and inhibitors of acid secretion. Appropriate salts of bismuth include bismuth aluminate, bismuth carbonate, bismuth subcarbonate, bismuth subgallate, bismuth subnitrate, and the like.

According to certain embodiments, the relative amount of the antacid component in the formulation is within the range of from about 5 to about 75% by weight and preferably from about 30 to about 60% by weight of the total antacid and antioxidant weight.

According to yet another embodiment, the antioxidant component comprises one or more ingredients selected from the group consisting of: polyphenols, buffering agents (e.g. ammonium carbonate, ammonium phosphate, boric acid, potassium citrate, potassium metaphosphate, potassium phosphate monobasic, sodium acetate, sodium citrate, sodium lactate solution, dibasic sodium phosphate and monobasic sodium phosphate) reducing agents (e.g. ascorbic acid and salts thereof, ascorbyl palmitates, thiols such as glutathione and derivatives thereof, glucosinolates, isothiocyanate, α-tocopherol, tocopherols and tocotrienols, carotenoids) and plant-derived antioxidants (e.g, polyphenols such as red wine polyphenols, plant extracts including but not limited to grape extracts, persimmon extracts, pomegranate extracts, bilberry extracts, blueberry extracts, rosemary extracts, sage extracts, oregano extracts, sapodila extracts, curcum extracts, ginger extracts, olive fruits and olive leave extracts, red beet extracts).

According to a currently more preferred embodiment, the antioxidant component is a polyphenol selected from the group consisting of: chalcones (e.g. phlonidzin); phenolic acid (e.g. caffeic acid); anthocyanins (e.g. malvidin-3-glucoside); flavonol (e.g. quercetin); flavanols (e.g. catechin); flavanones (e.g. hesperitin); flavanonols (e.g. astilbin); hydrolyzed tannins (e.g. punicalin); proanthocyanidin (e.g. epigallocatechin); phenolamine (e.g. dopamine, L-Dopa); lignans (e.g. curcumin); lignine; betalains (e.g. betanin); stilbenes (e.g. resveratrol); cyclic diuterpenes (e.g. carnosolic acid, carnosol); mono and sesquiterpenes (e.g. thymol); sesamolin (sesamol) and isoflavones (e.g daidzein, genistein).

According to certain embodiments, the relative amount of the antioxidant component in the formulation is within the range of from about 30 to 95%, preferably 35 to about 65% by weight and more preferably from about 40 to about 60% by weight of the final formulation.

According to yet another embodiment, the at least one pharmaceutically active ingredient is vulnerable to oxidative damage. According to yet another embodiment, the at least one pharmaceutically active ingredient is selected from the group consisting of: hormones and antibiotics.

According to yet another embodiment the composition is provided in any physical form suitable for oral administration, the composition having a physical form selected from the group consisting of: tablet, compressed tablet, spheroid, powder, capsule, suspension and liquid.

According to yet another aspect the present invention provides methods for systemic protection from oxidative damage. In alternative embodiments there are provided methods for protecting the GI tract from oxidative damage and further for preventing peroxidation and generation of peroxides and free radicals in the stomach. According to certain embodiment, the invention provides method for potentiating antioxidative activity.

According to one embodiment, the present invention provides a method for systemic protection from oxidative damage, comprising administering to a subject a composition consisting essentially of: (a) at least one antacid component in a dose sufficient to elevate the pH in the stomach; (b) at least one antioxidant component in a dose sufficient to decrease free radical generation in the stomach; and, optionally, (c) a carrier, diluent or stabilizer.

According to yet another embodiment, the method of the invention is for protecting the stomach and the esophagus from oxidative damage.

According to another embodiment, the present invention provides a method for inhibiting peroxidation reactions in the GI tract comprising administering to a subject a composition consisting essentially of: (a) at least one antacid component in a dose sufficient to elevate the pH in the stomach; (b) at least one antioxidant component in a dose sufficient to decrease free radical generation in the stomach; at least one carrier, diluent or stabilizer.

According to yet another embodiment, the present invention provides a method for attenuating generation of peroxides and free radicals in the GI tract comprising administering to a subject a composition consisting essentially of: (a) at least one antacid component in a dose sufficient to elevate the pH in the stomach; (b) at least one antioxidant component in a dose sufficient to decrease free radical generation in the stomach; and, optionally (c) at least one carrier, diluent or stabilizer.

The inventors previously disclosed (Kanner et al., ibid) that peroxidation in the stomach is continued even after a meal, under conditions that favor oxidation such as low pH and the presence of dissolved oxygen and optionally catalysts, such as ferrous ions. Thus, it is advantageous to apply the methods of the invention any time during the day in order to increase the antioxidative activity and to disintegrate free radicals and peroxides such as lipid peroxides.

According to one embodiment, the composition is administered to a subject before a meal or in parallel to a meal. According to an alternative embodiment, the composition is administered to a subject in need thereof several times a day.

According to another aspect, the principles of the present invention may be used for improving ulcer and ulcer related symptoms. Thus, the scope of the invention includes supplementing administration of an antacid by parallel or consecutive administration of an antioxidant, preferably an antioxidant which is compatible to the antacid.

According to a preferred embodiment, the composition is preferably administered orally as a nutraceutical consisting of essentially non-prescription active ingredients.

Other objects, features and advantages of the present invention will become clear from the following description and drawings.

DETAILED DESCRIPTION OF THE INVENTION

One of the major problems addressed by the present invention is the need to regulate gastric and esophagus acidity wherein on one hand gastric acidity is necessary for digestion, protection against pathogenic bacteria, stimulation of peristaltic movements and functions of the stomach and digestive system. On the other hand, over acidity is associated with inflammation, ulceration and cancer of the stomach and the esophagus. The presence of non-protected epithelial cells in the stomach and the esophagus is another factor, which contributes to ulceration processes and the concomitant painful symptoms and risks.

Radical production in the gastro-intestinal track is induced by numerous factors, such as restraint stress, spicy food diet, high-fat diet and ethanol consumption. These factors promote superoxide anion generation, hydroxyl radical production, lipid peroxidation, increased membrane microviscosity and increases in DNA fragmentation in the gastric mucosa cell (GC; Bagchi D et al. D.S. Dis. Sci 1999 44:2419-28). Nevertheless, stomach acidity is in fact facilitating and even amplifying peroxidation, which may be further catalyzed by met-myoglobin or iron ions. The cross reactions between lipid free radicals, generated during lipid peroxidation, and other food constituents dramatically enriches the range of cytotoxic and atherogenic compounds produced in the stomach such as peroxides, hydroperoxides, oxycholesterols, malondialdehyde, and hydroxy-alkyls. Hence, lipid peroxides are not only formed in foods, but may also be generated during digestion, especially in the gastric fluid, which contains absorbed oxygen and has a low pH suggesting that the human gastric fluid is an excellent medium for enhancing the oxidation of lipids and other dietary constituents (Kanner et al, ibid).

The present invention provides compositions and methods using same for potentiating antioxidative activity, for systemic protection against oxidative damage and for protecting epithelial cells in the GI tract from oxidative damage, such as the damage caused by free radicals and peroxides. The compositions of the present invention consist essentially of antacids, antioxidants and a pharmaceutically acceptable carrier, stabilizer or diluent.

Typically, antioxidants are added to pharmaceutical and nutritional compositions comprising antacids, in order to protect one or more of the active ingredients from oxidative damage. Such protection is commonly achieved using relatively low levels of antioxidants, in the range of a few percentages by weight of the final formulation. However, the compositions of the present invention comprise up to 50% antioxidants or even more for the purpose of protecting the stomach and esophagus from oxidative damage. Thus, in the presence of at least one additional pharmaceutical active ingredient or nutritional ingredient to the formulation of the invention the additional ingredient may be also protected from oxidative damage as a 'by-product' of the overall antioxidative activity.

Moreover, antioxidant potency with regard to its antioxidative activity is affected by environmental conditions. Under certain condition an antioxidant may function as a pro-oxidant. Specifically, an antioxidant is in fact more potent in mild acidic condition than in strong acidic conditions. Thus, for preserving the effective and valuable antioxidative activity of antioxidants in the stomach, such molecules should be protected from the acidic environment in the stomach. The formulations and method of the present invention provide a practical solution to this problem, by essentially consisting an antioxidant together with antacid.

The term "pharmaceutically acceptable carrier" refers to a carrier medium that does not interfere with the effectiveness of the biological activity of the active ingredient, is chemically inert and is not toxic to the patient to whom it is administered.

The present invention provides a formulation consisting essentially of antacid and an antioxidant component which generally exhibits at least two-fold of the antioxidative activity as compared with the antioxidative activity of a similar formulation devoid of the antacid component, suggesting synergistic connection between these two components.

The term "synergistic" as used herein refers to a combination which is more effective than the additive effects of any two or more single agents. A determination of a synergistic interaction between an antacid and an antioxidant such as a polyphenol, may be based on the results obtained from the ferrous ion oxidation-xylenol orange (FOX2) method as described in the Example section, infra. The results of these assays are analyzed using spectral analysis at 560 nm with $H_2O_2$ standard curve.

Another major problem addressed by the present invention is the two contradicting activities that are associated by antioxidants and pro-oxidation catalysts. The antioxidative activity of an antioxidant may be reversed to a pro-oxidative activity under certain environmental conditions. Antioxidants and pro-oxidation catalysts act as antioxidants in mild acidic condition rather than in strong acidic conditions. Thus, elevating the pH in the stomach by using antacids together with antioxidants, according to the present invention, enables manifestation of the desired pro-oxidative activity. In that sense, the synergism between the antacid and antioxidant component of the formulation of the invention may be interpreted as the protective role of the first component on the antioxidative activity of the latter component. The low pH in the stomach reduces the potent antioxidative activity of an antioxidant and further encourages oxidation. The addition of antacids to the acidic environment, in accordance with the principles of the invention, reduces the rates of oxidation in the stomach by elevating the antioxidative activity of the antioxidant.

An unexpected phenomenon established by the inventors of the present invention is that that in the stomach, generation or breakdown of peroxides by endogenous catalysts or catalysts obtained from food products, or components thereof, and food supplements can be selected by polyphenols and antacids. In other words, the appropriate combination of polyphenol and antacids can invert the catalyzed reaction from pro-oxidation to antioxidation consequently attenuating lipid peroxidation in the stomach. This principle was observed in a simulated gastric system comprising catechin or red wine polyphenols and metmyoglobin catalyst. At low acidic conditions, which were obtained by the addition of antacid to the system, the metmyoglobin catalyzed the breakdown of peroxides to zero, and completely prevented lipid peroxidation and β-carotene co-oxidation, as exemplified hereinbelow.

The terms "a gastric-simulating system" or "simulated gastric system" are interchangeably used herein to describe an experimental setup comprising components which simulate, in-vitro, the environment of the GI tracts or components thereto. In a particular example, a gastric simulating system may comprise the following components: HCl 0.1N and pepsin (Kanner et al. ibid).

The compositions of the present invention confer the following advantages over formulations of an antacid alone:

(I) as the protective and antioxidative activities of the present compositions are more effective, the compositions of the present invention may be administered less frequently than other antacids alone;

(II) as the protective and antioxidative activities of the present compositions are more effective, the compositions of the present invention may be administered at lower doses than antacids alone; and (III) the composition of the invention may consist of a lower total amount of antacid and hence using the composition of the invention diminishes the damaging side effects associated with relatively high levels of antacids.

The notable high antioxidative activity conferred in situ by the formulation of the present invention makes these formulations particularly suitable for preventing gastric and esophagus mucosa lesion and gastric or esophagus associated lesions and cancers that are caused inter alia by generation of free radicals and peroxides.

Antacids and Use Thereof for Gastric Acidity

Approximately 40% of the U.S. population experiences heartburn at least once a month, and up to 7% experiences heartburn daily. Heartburn is the most common clinical manifestation of gastro esophageal reflux disease (GERD) in human. Most people with GERD self-treat the disorder by avoiding foods that seems to aggravate symptoms, life-style alteration and acid suppressors medications such as classical antacid, proton pump inhibitors and acid-suppressor $H_2$-receptor antagonists.

Physiologically, gastric acidity is necessary for food digestion and protection against pathogenic bacteria and even cancer. Thus, decreasing gastric acidity confers damaging side effects, namely, increased risk of imbalanced gastric flora (increased *Helicobacter pylori*), inflammation, and cancer of the stomach and esophagus.

However, over acidity is also known as a risk factor for stomach ulceration and stomach esophagus cancer. Common methods for reducing gastric acidity involve using agents that are capable of increasing the pH of the stomach, also termed herein "antacid". Surgical approaches for treating severe heartburn were found less effective than oral administration of antacid.

Clinical conditions typically regulated by antacids are:

1) Heartburn: Heartburn is commonly described as burning feeling in the chest after a meal or when reclining. It may also appear in the course of exercise. The cause of pain evolves from a back flux of the stomach acid fluids into the esophagus. During normal food consumption food travels from the mouth down the esophagus through a one-way valve, the lower esophageal sphincter (LES) which is the opening to the stomach. It normally opens only upon swallowing, thus enabling food to enter the stomach, and then it quickly closes.

In the event of access acidity or if the LES in not functioning properly, food and stomach acidic fluids may reflux back into the esophagus. This fluid reflux irritates the lining cells of the esophagus and causes heartburn. In cases where the stomach cannot prevent such reflux, the heartburn may worsen.

2) Stomach ulcer: A stomach gastric ulcer is a raw area or open sore that develops in the layer of cells lining the stomach. Another layer of cells that produce mucus normally protects the lining layer. The mucus prevents the stomach from being injured by stomach acidic fluids. When the protective layer is damaged, an ulcer may be generated.

Stomach ulcer is a major problem in racehorses and foals. Studies in England, Ireland, Hong Kong and the United States report that 80-90% of racehorses in training, 84% of yearlings and 51% of foals have stomach ulcers. Other research found that 50% of ponies on concentrates had ulcers, whereas ponies on hay diets did not. In addition, 30% of death incidences in foals between 1 and 4 months of age, are related to stomach ulcers. The period of highest risk for developing ulcers is from 2 days to 8 weeks after birth, especially in foals with diarrhea. The two major causes of gastric ulceration in racehorses and foals are: (1) reduced ability of the stomach to defend itself against gastric acid and digestive enzymes. Stress reduces normal protective mechanisms within the stomach. The major risk period is between 1 and 3 months of age, that is, before foals have begun eating sufficient solid food for saliva production to buffer stomach acid production, and (2) Prolonged exposure of the stomach to high acid levels. High acid levels result from modern feeding practices. Both fasting and high grain diets predispose to gastric ulceration. Horses and ponies in stables and those on high raw grain diets have more ulcers than those at pasture or on hay diets.

3) GERD: Gastroesophageal reflux disease (GERD). This clinical condition is not only unpleasant, but may also put a subject in a risk for Barrett's esophagus which is strongly related to incidences of adenocarcinoma of the esophagus. Heartburn is the most common clinical manifestation of GERD. For most people, GERD is more of a nuisance than a threat, as in the majority of the patients suffering from GRED ulcer, together with the subsequent risk of bleeding or stricture formation, is not developed in the esophagus. Other ulcer-associated problem are related to the upper-airways, including asthma, aspiration pneumonia, or chronic cough. Only 5% to 10% of patients with complaints of reflux have demonstrable endoscopic esophagitis.

4) Injury of esophageal epithelial cells: injury to esophagus as opposed to that of stomach and duodenum is generated due to one or more of the following factors: (i) lack of mucus and bicarbonate secretion by surface epithelial cells; (ii) lack of defensive enhancement by prostaglandin release; (iii) lack of an effective mucus cap after injury; and (iv) lack of capacity to rapidly heal erosions by the process of epithelial restitution.

5) Gastro-esophageal cancer: It is common knowledge that subjects suffering from chronic heartburn and acid reflux are prone to develop esophagus cancer, including adenocarcinoma, the most lethal form of esophageal cancer. Without limitation, it is assumed that because the esophagus is not protected with a lining protective layer of cells, like the stomach, stomach acid fluids irritates the lower esophagus and, over time, trigger pre-cancerous changes in this site that may progress into cancer. Whereas the overall risk for esophageal cancer is still very low (about 12,500 per year as compared with 20 to 30% of the U.S. population reporting heartburn at least once monthly), it grows among white men. Barrett esophagus which as mentioned above is a complication of GERD is strongly correlated with esophageal cancer.

The term "antacid" as used herein refers to an agent which is capable of reducing gastric acidity with the proviso that this agent is approved for clinical or veterinary use. Antacid are typically orally administered alkaline drugs. Antacids are capable of raising gastric pH. In certain embodiments, antacids are capable of raising gastric pH 4.0 or even above pH 4.0. The duration of action of soluble antacids is usually longer than that of insoluble antacids.

It is suggested that classical antacid exerts its activity through the binding of the antacid cation with the chloride anions of HCl in the stomach, to form a salt. It is suggested that this mechanism leads to partial neutralization of gastric hydrochloric acid and inhibition of the proteolytic enzyme, pepsin. Each cation salt has its own pharmacological characteristics that are important for determination of which product can be used for certain indications.

Classical antacids may be divided into families, as follows:

(a) Aluminum hydroxide: non-systemic, considerably weak and raises pH of the stomach to 4-5 pH units. Also known to exhibit delays gastric emptying rate and may cause constipation.

(b) Calcium carbonate (e.g. Tums®): non-systemic, may raise the pH of the stomach to 7.0, encourages gastric emptying. May cause more "acid rebound" than other antacids.

(c) Magnesium hydroxide: non-systemic, used as an antacid and cathartic, raises pH of stomach contents to 9, increases gastric emptying rate. Should not be taken by a subject suffering from renal difficulties.

(d) Sodium bicarbonate (e.g. Alka Seltzer®): systemic potent antacid that increases gastric emptying rate. This family of antacids may not be recommended for co-administration with other drugs due to its systemic effect.

(e) Natural antacids (e.g. Gastro-AD™, Prelief®): products obtained by fermentation of bacteria which are typically added to the food or consumed together with food.

(f) Tamer combination of the same natural active ingredients including calcium carbonate, potassium and magnesium hydroxide are devoid of aluminum, sodium, gelatin, and the like and are more potent than common antacids, such as Tums®, Maalox®, and Mylanta®.

An important group of antacids that may be used according to the principles of the present invention is the group of proton pump inhibitors. In contrast to the activity of classical antacids, proton pump inhibitors work by completely blocking the production of stomach acid by inhibiting (shutting down) a system in the stomach known as the proton pump. This system is also known as 'hydrogen-potassium adenosine triphosphate enzyme system'. Proton pump inhibitors are used to heal stomach and duodenal ulcers. This includes stomach ulcers caused by taking nonsteroidal anti-inflammatory drugs. They are also used to relieve symptoms of oesophagitis (inflammation of the oesophagus or gullet) and severe gastro-oesophageal reflux, a condition where acid leaks up from the stomach into the gullet.

Substituted benzimidazoles are substituted sulfoxides which are potent inhibitors of gastric acid secretion. Such substituted sulfoxides are described for example in European Patent No. 0005129 B1. These compounds are susceptible to degradation and/or transformation in both acid and neutral media. The acidic decomposition of these acid labile compounds is due to an acid catalyzed reaction described by G. Rackur et al., in Biochem. Biophys. Res. Commun. 1985: 128(1). P477-484.

In combination with certain antibiotics (e.g. amoxycillin and clarithromycin), proton pump inhibitors are used for avoiding *Helicobacter pylori* infection.

Proton pump inhibitors are also the drugs of first choice for a rare condition called Zollinger-Ellison syndrome. This is a condition where a tumor in the pancreas causes too much stomach acid to be produced and so leads to severe stomach ulceration.

Treatment with proton pump inhibitors may be involved with several side effects. The most common side effects are diarrhoea, nausea, constipation, wind, abdominal pain and headaches. Very rarely they can also cause allergic reactions, itching, dizziness, swollen ankles, muscle and joint pain, blurred vision, depression and a dry mouth. A problem that can occur with long-term use of proton pump inhibitors is stomach infections. Stomach acid helps to kill microscopic organisms (microbes) such as bacteria in the stomach. Because proton pump inhibitors completely stop acid production using them can lead to a growth of microbes in the stomach.

Use of proton pump inhibitors may have to be strictly monitored in subjects suffering from liver or kidney problems, or that are pregnant or breastfeeding. Additionally, it is not recommended to use proton pump inhibitors in conjunction with other medicines or herbal remedies. For example, the effects of phenyloin (an epilepsy medicine) and warfarin (for preventing blood clots) are affected by some of the proton pump inhibitors. Furthermore, the absorption of the antifungal drugs ketoconazole and itraconazole are reduced by proton pump inhibitors and the breakdown of diazepam in the body may be blocked by some of the proton pump inhibitors so that there is an increased effect of diazepam.

Yet another group of antacids that may be used in the context of the present invention is that of "$H_2$-receptor antagonists" or "$H_2$ antagonists". The activity of these compounds is related to histamine signaling. Histamine is a naturally produced molecule that stimulates certain cells in the stomach to produce acid by attaching, or binding, to their $H_2$ receptors. As a result of Histamine binding to the $H_2$ receptors cellular acid production is enhanced. The $H_2$ antagonists function by binding to the $H_2$ receptors without triggering acid production.

The $H_2$ antagonists are taken to heal stomach and duodenal ulcers including ulcers caused by taking a nonsteroidal anti-inflammatory drug. In order to avoid ulcer-reoccurrence treatment with $H_2$ antagonists may be extended to long-term periods in a reduced dose. The $H_2$ antagonists can also be used to relieve indigestion, heartburn and gastro-oesophageal reflux (GERD), a condition caused by acid leaking up from the stomach into the bottom of the gullet. One of the $H_2$ antagonists is also available in a form that contains bismuth citrate (ranitidine bismuth citrate). This is used, along with other drugs, to avoid *Helicobacter pylori* infection.

The most common side effects associated with treatments with $H_2$ antagonists are diarrhoea and other digestive disturbances, headache, dizziness and tiredness, and hair loss with cimetidine and sweating with nizatidine.

Cimetidine should be avoided in people taking on warfarin, phenyloin and other drugs for epilepsy, theophylline or aminophylline, and some drugs for abnormal heart rhythms because it can affect the way the body breaks them down.

Antacid treatment is usually given via oral administration using orally suitable forms such as tablets or syrups.

Mild incidences of heartburn respond well to antacid medications, by relieved heartburn and decrease in the associated pain and nuisance of reflux esophagitis. Relief with liquid antacids is most often achieved faster with the corresponding solid alternatives, such as a tablet. Antacids have been used for duodenal and gastric ulcers, stress gastritis, gastro-esophageal reflux disease, pancreatic insufficiency, non-ulcer dyspepsia, bile acid mediated diarrhea, bile mediated reflux, constipation, osteoporosis, urinary alkalization and chronic renal failure as a dietary phosphate binder. Histamine $H_2$-receptor antagonists and proton pump inhibitors has significantly reduced usage of classical antacids for duodenal and gastric ulcers and gastro-esophageal reflux disease.

However, antacids can still be useful for stress gastritis and non-ulcer dyspepsia. Antacids are likely to continue to be used for non-ulcer dyspepsia, minor episodes of heartburn (gastro-esophageal reflux disease) among other similar indications.

Antacids may also be given in combination with simethicone (also known as tradenames: Gas-X®, Mylicon®, Phazyme® and SonoRX®), which may relieve the symptoms of flatulence, and also to treat stomach or duodenal ulcers. With larger doses magnesium hydroxide (magnesia) and magnesium oxide antacids produce a laxative effect. Some antacids, e.g. aluminum carbonate and aluminum hydroxide, are used with a low-phosphate diet to treat hyperphosphatemia, and can also be used with a low-phosphate diet to prevent the formation of renal calculi.

Although most adverse effects from antacids are minor with periodic use of small amounts, when large doses are taken for long periods of time, significant adverse effects may occur (see for example, Maton et al, Drugs 1999, 57:855-70). Several disadvantages are associated with use of antacids:

A. Acid rebound. All antacids cause acid "rebound". Although the use of antacids contributes to immediate relief of the over acidity sensation, the duration of the effect is sometimes limited and only relieves the acidity in the lower esophagus, where the sensitive lining tissues in the stomach are not protected by the treatment. As a result, antacid treatment is extended to long time periods while not providing the required complete healing effect. This may result in acidity "rebound" intensive use of antacids.

The terms "rebound" or "acid rebound" as used herein interchangeably in reference to the limited effectiveness of various antacids in reducing gastric acidity.

B. Cost effectiveness. Intensive non-efficient use of antacid is costly as it involves medical appointments, the costs of prescription and medications and indirect costs such as absence from work.

C. Cross-drug interaction. Antacid interaction with other drugs is well documented, though it may be avoided by rescheduling administration times. However, rescheduling administration times can be inconvenient and may discourage compliance of the complete treatment with all medications. For example, fluoroquinolones potency is reduced when co-administered with antacid. Co-administration of cellulose sodium phosphate together with calcium-containing antacids may reduce the potency of cellulose sodium phosphate. Magnesium-containing antacids may also prevent effective drug activity. Aluminum-containing antacids may reduce the effects of tetracyclines and isoniazid antibiotics (also known as INH®, Laniazid® and Nydrazid®). Antacids may also decrease the activity of Ketoconazole, Mecamylamine and Methenamine. Sodium polystyrene sulfonate resin (SPSR) may decrease the effectiveness of antacids.

D. Promoting the activity of cancer-related bacteria. Antacid treatments was shown to correlate with a growth of *Helicobacter pylori* ulcer bacteria, which is known to be associated with cancer. It is speculated that the lower acidity produced by the antacid promotes the growth of the bacteria. *Helicobacter pylori* (*H. pylori*) has been identified in the pathogenesis of chronic active gastritis and peptic ulcer disease and is epidemiologically associated with gastric cancer and lymphoma. It has been shown that production of reactive oxygen species (ROS) in cultured gastric adenocarcinoma cells (ATCC CRL/1739) is enhanced by at least 3.5 folds in the presence with *H. pylori* and in comparison to a similar culture devoid of *H. pylori*. *H. pylori* was also associated with DNA fragmentation in gastric mucosal cells. The cytotoxin 87-kDa rich-*H. pylori* strain 60190 induced greater production of ROS and DNA fragmentation in mucosal cells as compared to the supernatant preparation from *H. pylori* strain 60190-v1, in which the cytotoxin gene has been disrupted suggesting that *H. pylori* damage is related to the cytotoxin induced ROS (see for example, Dig. Dis. Sci. 2002, 47:1405-12).

E. Powerful antacids might increase cancer risks. The gastrin hormone in the stomach stimulates the production of gastric acid. Certain conditions that increase the gastrin hormone in the stomach also increase the risk of stomach cancer.

Previous research has shown that strong acid-reducing medications increase the level of gastrin in the stomach.

F. Increased inflammatory response. It was found that extensive treatment with several antacids elevates significantly the bacteria populations and causes the development of stomach inflammation. This phenomenon may be however eliminated by co-administration of antibiotics with antacids.
Protection of the Gastric System by Antioxidants and Antioxidative Mechanisms Free radical production occurs continuously in all cells as part of normal cellular function. However, excess free radical production originating from endogenous or exogenous sources might play a role in many diseases.

Human gastric mucosa contains a highly active peroxidase in addition to the myeloperoxidase contributed by neutrophils. The activity of endogenous peroxidase, a major $H_2O_2$ metabolizing enzyme, was recently reported showing its critical role in controlling oxidative damage in gastric mucosa. When myeloperoxidase level increases due to neutrophil accumulation, gastric peroxidase (GPO) level decreases significantly. This leads to further accumulation of endogenous $H_2O_2$ that can cause more oxidative damage and aggravate the ulcer. Also mucosal total superoxide dismutase (Mn and Cu—Zn SOD) level decreases significantly under accumulation of reactive oxygen metabolites (ROM), leading to increased accumulation of $O_2$. Gastric ulcer is associated with oxidative damage of the mucosa as evidenced by significant increase in lipid peroxidation, protein oxidation, and thiol depletion indicating accumulation of ROM. It is also recognized that many other diseases are caused or provoked by a free radical oxidation mechanism e.g. cancer, cataracts and diabetes among others.

Potent antioxidants are capable of attenuating and even preventing the formation of radicals by scavenging them, promoting their decomposition and reversing the harmful actions of reactive oxygen and nitrogen species, which are generated in vivo. One of the major damaging effect of reactive oxygen and nitrogen species is destruction of DNA, lipids, proteins, and other biomolecules. Endogenous antioxidant defenses, such as superoxide dismutases, $H_2O_2$-removing enzymes and metal binding proteins, are inadequate for a complete prevention of the damage associated with the reactive species, and thus an exogenous supply of antioxidants is important. Many dietary compounds have been suggested to be important antioxidants, including vitamins E and C and especially flavonoids. Some antioxidants can exert pro-oxidant effects in vitro, but their physiological relevance is uncertain.

In considering the biological importance of dietary antioxidants, attention was usually focused on those that are absorbed through the gastrointestinal (GI) tract into the rest of the body. Recent publications raised the argument that the high levels of antioxidants present in certain foods (fruits, vegetables, grains) and beverages (e.g. green tea) play an important role in protecting the gastrointestinal tract itself from oxidative damage, and in delaying the development of stomach, colon and rectal cancer. Carotenoids and flavonoids do not seem to be as well absorbed as vitamins C and E. Hence their concentrations can be much higher in the lumen of the GI tract than in the plasma or other body tissues, enabling their antioxidative action in the GI tract. Additional protective mechanisms of these dietary constituents (e.g. effects on intercellular communication, apoptosis, cyclooxygenases and telomerase) may also be important.

Polyphenols is a class of substituted phenolic compounds that are also known as flavanols or catechins and are commonly found in plant extracts. Polyphenols occur abundantly in red wine and consist of a large number of different chemical substances of varying molecular weights. The chief polyphenol components of grapes and wine, and their concentrations. See for example U.S. Pat. No. 6,642,277. Among the polyphenols are the following classes: flavonoids (a term often used to denote polyphenols in general, but more commonly in Europe to denote only the flavones), the flavanols, proanthocyanidins (also called procyanidols, procyanins, procyanidins and tannins) and anthocyanins. Within the general term "polyphenols" are included the dihydroxy- or trihydroxy benzoic acids and the phytoalexins, a typical example of which is resveratrol.

Polyphenols may conveniently be obtained from red wine, grape juice, or other polyphenol-containing liquids by absorption onto a chromatographic resin column, with elution of the polyphenol-enriched fraction from the column (typically following a washing step) by use of a 40-80% ethanol eluent, or other suitable organic solvent (such as methanol, acetone, ethyl acetate, dimethylene chloride, and chloroform, which may be in aqueous solution). The organic solvent is preferably relatively volatile (i.e. having a boiling point of between 30 and 85° C. at 760 mm Hg pressure) and so readily driven off, to leave a substantially dry (i.e. less than 10% w/w $H_2O$) solid composition comprising polyphenols. Such a method may successfully be used to obtain a total polyphenol pool from red wine.

Alternatively, polyphenols may be obtained from red wine, grape juice, or other polyphenol-containing liquid by solvent extraction using a suitable organic solvent immiscible with the wine or other liquid. Alternatively, polyphenols may be obtained from polyphenol-containing solids by solvent extraction (typically extraction with an organic solvent such as ethanol or ethyl acetate) the solids can then be separated from the solvent by filtration or centrifugation. The solvent may then be evaporated to leave a substantially dry, solid composition comprising polyphenols.

A number of compositions are publicly available which are prepared from wine or grape by-products and which allegedly contain polyphenols (albeit at quite low levels in some of the compositions). Among them is French Paradox™ made by preparing an extract from marc (the grape skin waste remaining after wine fermentation). Most of the polyphenols present in the grape skins are alcohol-soluble, and so tend to be extracted into the fermenting wine. Hence, French Paradox™ capsules have actually rather low polyphenol content. Other publicly available compositions include an anthocyanin-containing powder (obtainable from Sefcal™) made from a grape skin extract, and which is used as a food colorant, and a pro-anthocyanidin-containing composition (Endotelon™) prepared from grape seeds.

Quercetin is a naturally occurring bioflavonoid with strong antioxidant activity. The antioxidant activity of quercetin protects the gastrointestinal tract in several ways:

(I) Quercetin prevents oxidation of lipids. The gastrointestinal tract has an increased exposure to oxidative stress due in part to the low pH therein. It is important to protect the lipid bilayer of the cell wall of the gastrointestinal tract as these cells are an important component of the immune system.

(II) Quercetin prevents the depletion of glutathione in the cells of the intestinal tract. Glutathione is a co-substrate for the antioxidant enzymes glutathione peroxidase and glutathione reductase. By preserving the accumulation of glutathione, quercetin protects metabolic activity and cellular structure of these highly vulnerable cells from the damage caused by toxic free radical. Vitamin C synergistically improves the ability of the quercetin to preserve glutathione.

(III) Quercetin increases mucus secretion from gastric cells. The mucus polysaccharide provides a protective buffering layer for the gastric cells from the low pH of the stomach. Such reduced contact prevents or reduces the occurrence of gastric lesions.

(IV) Quercetin induces antispasmodic activity that prevents uncontrolled peristaltic activity such as the activity that is associated with diarrhea. The reduced excretion of the intestinal contents provides benefit to the gastrointestinal tract by preventing overproduction of cellular protective materials.

(V) Quercetin reduces the immune response to allergens by inhibiting IgE-mediated release of molecules from mast cells. Quercetin also inhibits IgG-mediated histamine release. Furthermore, quercetin is a potent inhibitor of lipoxygenase, which metabolizes arachidonic acid as the first step towards pro-inflammatory arachidonic acid mechanism. These activities of quercetin provide a wide protection of the GI tract against gastric lesions. These activities are enhanced in the presence of vitamin C and prevent from antigenic proteins and other antigenic compounds from entering to the body.

Anthocyanosides, also known as Bilberry anthocyanoside, is a family of plant-derived polyphenols. They are sometimes called anthocyanidins. Typical examples are: cyanidin (hydroxylated at positions 3, 5, 7, 3', 4'), delphinidin (hydroxylated at positions 3, 5, 7, 3', 4', 5') and pelargonidin (hydroxylated at positions 3, 5, 7, 3'). The hydroxyl groups are usually glycosylated and/or methoxylated (e.g. malvidin at 3', 5'). Antocyanosides are used for treating inflammation and ulcer. Administration of a Bilberry anthocyanoside extract induces reduction of inflammation, in-vivo. It has been suggested that this polyphenol may also reduce platelet aggregation, probably by increasing release of prostacyclin, a potent blood vessel dilating and platelet anti-aggregation factor. Orally administered bilberry anthocyanosides prevents and even cures ulcer activity in various experimental models of gastric ulcer without affecting gastric secretion. This activity can be attributed, at least partly, to an increase in gastric mucus.

Consumptions of polyphenols derived from green tea were associated with reduced risk of stomach cancers and esophagus cancers. An epidemiological study conducted in Shanghai, China (1986) among 18,244 men of 45 to 64 years indicated that only half of the 'heavy' tea-drinkers developed cancer of the stomach or esophagus as compared with 'light' tea drinkers. Among different kinds of tea, the green tea contains the highest levels of the antioxidants polyphenolic molecules: catechins. Catechin was shown to inhibit the growth of tumor cells and to protect healthy cells from damage associated with cancer. U.S. Pat. No. 6,652,890 discloses methods and compositions of treating cancer or solid tumors utilizing catechins. The compositions of catechins include epigallocatechin gallate (EGCg) the major catechin in green tea, epicatechin (EC), epicatechin gallate (ECG), epigallocatechin (EGC).

Case-control study in Spain, on 354 cases of gastric cancer and 354 controls, supports the hypothesis that the protective effect of fruit and vegetables against gastric cancer could, in part, be due to the presence of flavonoids. In addition, a review of the scientific literature on the relationship between vegetable and fruit consumption and risk of cancer, resulted from 206 human epidemiological studies and 22 animal studies showed evidence for a protective effect of high vegetable and fruit consumption against cancers of the stomach, esophagus, lung as well as oral cavity and pharynx, endometrium, pancreas, and colon. Substances present in vegetables and fruit that may help protect against cancer, and their mechanisms, were also briefly reviewed; these included dithiolthiones, isothiocyanates, indole-3-carbinol, *allium* compounds, isoflavones, protease inhibitors, saponins, phytosterols, inositol hexaphosphate, vitamin C, D-limonene, lutein, folic acid, beta carotene, lycopene, selenium, vitamin E, flavonoids, and dietary fiber.

Numerous antioxidants, derived from medicinal plants, were shown to have gastric cyto-protective activity. Analyses of the chemical content of medical plants extracts showed that most of these type of plants mainly contains the following molecules: tannins, saponins, flavonoids and coumarins. A common family of medicinal plant is the *Stachytarpheta cayennensis*. Extracts of plants from this family showed notable anti-secretion and anti-ulcer activities. Cholinergic and histaminergic stimulation of acid secretion were similarly reduced by these extracts suggesting inhibition of common steps in both pathways, possibly at the level of histamine release/H2 receptor interaction, or at the proton pump.

Among the various beneficial activities attributed to polyphenols, inhibition of gastric H+, K(+)-ATPase by was also observed. Gastric H+, K(+)-ATPase plays a pivotal role in the final step of gastric acid secretion and some flavonoids were found to inhibit the activity of this enzyme.

Several types of flavonoids and their metabolites, such as Ponciretin, hesperetin, naringenin and diosmetin, were also capable of presenting anti-*Helicobacter pylori* activity, in vitro.

Distribution pattern of flavonoids in the gastrointestinal lumen and wall was shown to be accompanied by partial deglycosylation that began in the stomach where at first quercetin and later apigenin, chrysoeriol and isorhamnetin aglycones were detected.

Antioxidants are advantageous over antacids in preventing reflux oesophagitis. Preliminary experiments in rats having surgically-induced reflux oesophagitis indicated that wormwood, which has antioxidant properties, successfully managed reflux esophagitis as compared to treatment with ranitidine (a common acid suppressant anti-secretory agent). Treatment with wormwood resulted with less severe blistering, lower levels of inflammation and more extensive healing.

Another protective effect of antioxidants is their ability to prevent gastropathy induced by non-steroidal anti-inflammatory drugs (NSAID). NSAID treatment is known to induce, in a large percentage of the subjects treated with these drugs these, gastric ulcers and related complications, a condition which is also known as "NSAID gastropathy". NSAID gastropathy differs from classic peptic ulcer disease in many ways, and traditional peptic ulcer therapy is largely ineffective in preventing NSAID-induced gastropathy. The prostaglandin misoprostol has been shown to be effective and is approved for the prevention of NSAID gastropathy. Common NSAIDs include phenylbutazone ('bute') and flunixin meglumine (Banamine™). NSAIDs act by interrupting the production of prostaglandins. One particular prostaglandin, PgE2, plays an important role in preventing gastric ulceration. PgE2 exerts its preventive activity by reducing gastric acid production and by increasing blood flow to the gastric epithelium.

U.S. Pat. No. 6,365,184 discloses an oral pharmaceutical dosage form comprising an acid susceptible proton pump inhibitor and one or more NSAIDs in a fixed formulation, wherein the proton pump inhibitor is protected by an enteric coating layer. The pharmaceutical dosage form is especially useful in the treatment of gastrointestinal side-effects associated with NSAID treatment.

Yet another protective effect of antioxidants is their ability to inhibit nitrous acid-dependent tyrosine nitration and DNA base deamination. A vast range of plant polyphenol constituents was shown to prevent damage mediated by acidic nitrite. The epicatechin/gallate family of flavonols, constituents of green tea, red wine, etc., demonstrated the most extensive inhibitory properties against both tyrosine nitration and base deamination. The ability of plant polyphenols to scavenge reactive nitrogen species derived from acidic nitrite may explain their protective effects against gastric cancer.

Pharmaceutical Compositions and Modes of Administration

The formulations of the invention may be formulated into pharmaceutical preparations for administration to a subject as a medicament or as food supplements or as food fortifying ingredients. The formulations may be specifically administered in the context of pharmaceutical preparations for treatment of gastric- and esophagus-associated diseases. In a preferred embodiment, the subject is a mammal.

According to one embodiment, the present invention provides a formulation consisting essentially of:
 (a) an antacid component;
 (b) an antioxidant component;
 (c) a pharmaceutically acceptable carrier; and, optionally,
 (d) at least one active pharmaceutical ingredient.

According to another embodiment, the pharmaceutically acceptable diluent, stabilizer or carrier comprises at least one substance selected from the group consisting of: water, organic solvent, inorganic solvent, buffering agent, acidifying agent, alkalizing agent and alcohol denaturant.

According to one embodiment, the composition of the invention may further comprise at least one of the following ingredients: filler (e.g. xylitol, mannitol), disintegrant (e.g. crosspovidone), anticaking agent (e.g. silicon dioxide), film coating (e.g. polymethacrylates), coating solution (e.g. denatured ethanol), binder (e.g. bentonite, corn starch), stabilizer for or for solid forms, entericoating polymer, sweetening agent (e.g. aspartame), glidant (e.g. silicon dioxide), flavor, color (e.g. titanium dioxide), lubricant and plasticizer (e.g. triethylcitrate).

Formulations according to the present invention may comprise any conventional carrier or adjuvant used in pharmaceuticals, personal care formulations and compositions or veterinary formulations. These carriers and adjuvants include, the following:
 (i) Acidifying agents.
 (ii) Alcohol denaturants, such as, methyl isobutyl ketone and sucrose octacetate.
 (iii) Alkalizing agents.
 (iv) Antifoaming agents, e.g. dimethicone and simethicone.
 (v) Antimicrobial preservatives, such as, benzalkonium chloride, benzalkonium chloride solution, benzelthonium chloride, benzyl alcohol, butylparaben, cetylpyridinium chloride, chlorobutanol, chlorocresol, cresol, ethylparaben, methylparaben, phenol, phenylethyl alcohol, propylparaben and propylparaben sodium.
 (vi) Plasticizers, e.g. castor oil, diacetylated monoglycerides, diethyl phthalate, glycerin, mono- and di-acetylated monoglycerides, polyethylene glycol, propylene glycol, triacetin and triethyl citrate.
 (vii) Solvents, for example, acetone, alcohol, diluted alcohol, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil and water.
 (viii) Sorbents, such as, powdered cellulose, charcoal, purified siliceous earth or carbon dioxide sorbents (e.g. barium hydroxide lime, soda lime).
 (ix) Stiffening agents, for example, hydrogenated castor oil, cetostearyl alcohol, cetyl alcohol, cetyl esters wax, hard fat, paraffin, polyethylene excipient, stearyl alcohol, emulsifying wax, white wax and yellow wax.
 (x) Suppository bases, e.g., cocoa butter, hard fat and polyethylene glycol.

Compositions comprising a compound of the invention formulated in a compatible pharmaceutical carrier may be prepared, packaged, and labeled for treatment of the indicated disease, such as sarcomas and carcinomas (e.g., fibrosarcoma, colon carcinoma, gastric carcinoma, adenocarcinoma, papillary carcinoma, papillary adenocarcinomas, epithelial carcinoma, gastro-esophageal cancer), GERD disease, stomach or duodenal ulcer, heartburn, peptic ulcer disease, chronic active gastritis, *Helicobacter pylori* ulcer, gastric inflammation and reflux oesophagitis.

The formulations and their physiologically acceptable carrier may be formulated for oral administration. For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates).

The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., talc or silica); disintegrants (e.g., potato starch or sodium starch glycolate); or wetting agents (e.g., sodium lauryl sulphate). The tablets may be coated by methods well-known in the art. In a preferred embodiment, the pharmaceutical composition may take the form of a capsule or powder to be dissolved in a liquid for oral consumption.

The compositions of the invention may be in any edible form or part of a food products such as a candy bar, chocolates and the like.

Novel pharmaceutical compositions for acid labile substances, particularly proton pump inhibitors such as lansoprazole or omeprazole, as well as for methods of making such are disclosed in U.S. Pat. No. 6,296,876.

According to another embodiment, the antioxidant compound is a polyphenols, such as a catechin. Catechins may be combined with any antacid in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g. water, glycols, oils, alcohols, flavoring agents, preservatives, coloring agents, and the like; in the case of oral liquid preparations, e.g., suspensions, solutions, elixirs, liposomes and aerosols; starches, sugars, micro-crystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% (w/v), normal saline or other solutions. The total dose of the catechins and antacids may be administered in a vial of intravenous fluid, e.g., ranging from about 0.01 to about 1000 mg per kg body weight of catechins. The volume of dilution fluid will vary according to the total dose administered and over the length of the period of time of administration.

Various aspects and embodiments of the present invention are illustrated in the following examples. It will be appreciated that modification of detail may be made without departing from the scope of the invention.

EXAMPLES

Materials and Methods

Metmyoglobin (metMb, from horse skeletal muscle), soybean lipoxygenase (type I-B), β-carotene, linoleic acid, Tween 20, butylated hydroxytoluene (BHT), catechin, pepsin (A, from porcine stomach mucosa), ferrous ammonium sulfate. Xylenol orange, and triphenylphosphine (TTP) were obtained from Sigma Chemical Co. (St. Louis, Mo., USA). Sodium chloride, hydrogen peroxide (30%) and L (+)-ascorbic acid (AA) were obtained from Merck (Darmstadt, Germany). Ferric chloride (Fe) was obtained from Riedel-de-Haen (Hannover, Germany). Sodium borohydride was obtained from BDH (NJ, USA). Human gastric fluid (HGF) was collected, with consent, from a fasting woman (age 25) during regular gastric endoscopic tests, and was kept at −80° C. Small slices grilled turkey meat was kept at −80° C. Simulated gastric fluid (SGF) was freshly prepared according to the U.S. Pharmacopoeia.

Spectroscopic measurements: The presence of hydroperoxides was determined by means of the ferrous ion oxidation-xylenol orange (FOX2) method (Nourooz-Zadeh, J. Methods Enzymol. 1999, 300: 58-62.) including spectral analysis at 560 nm with $H_2O_2$ standard curve.

Hydroperoxides measurement in linoleic acid emulsions: Catechin was dissolved in 10% ethanol in water and the reaction tubes were incubated in triplicate in a shaking bath at 37° C. for 180 min. Samples of 25 or 50 µl were taken from the reaction tubes during the incubation and added to 475 or 950 µl, respectively, of FOX2 reagent. Before each experiment, old stock solution of linoleic acid was mixed with fresh solution in order to maintain an accurately consistent initial level of hydroperoxides.

The presence of metMb, Fe, AA, wine, or catechin, at the concentrations used in the experiments, did not interfere with the FOX2 assay.

Example 1

Hydroperoxides Measurement in Turkey Muscle Tissue

Muscle tissue was ground with three parts of liquid, containing SGF with red wine, or ethanol solution or water as controls, for 1 min in a laboratory blender (Waring®, CT, USA) and adjusted to pH 3.0. The wine was diluted with 12% ethanol solution, so that the ethanol content (final concentration 6%) was equal in all treatments, except for the water control.

The meat-liquid mixture in each treatment was divided among several tubes and incubated in a shaking bath at 37° C. for 180 min. At five times points, the hydroperoxides in the samples were extracted by 10-fold dilution in methanol under slow stirring for 15 min, following paper filtration (cat. No. 1442, Whatman®, England). Samples, 100 µl, of the filtered solution were subjected to the FOX2 assay, which included TTP reagent controls, in order to prevent potential interference from ferric ions and the red wine pigments.

Figure 1:
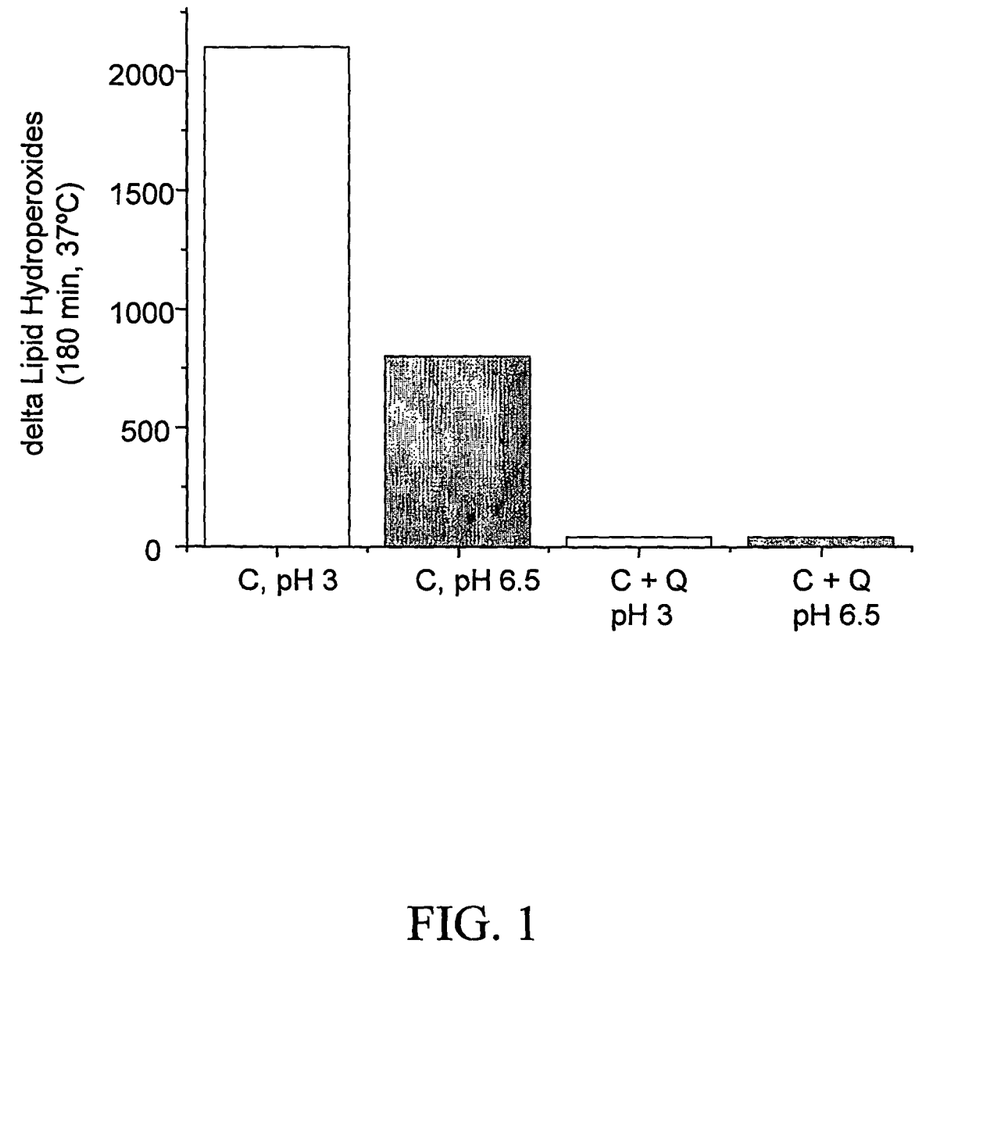
FIG. 1 demonstrates pH dependency of lipid peroxidation in oxidized muscle in control samples (C) or in samples containing quercetin (Q; 2 mM).

The heated red turkey meat was found to contain about 180 µLM hydroperoxides and malondialdehydes, a concentration which is 10-20 times higher than that in the fresh muscle (FIG. 1).

In addition to the control samples, that is samples that were devoid of antacid, the heated red turkey muscle was ground in the presence of an antacid that elevated the pH to 6.5. An antioxidant (catechin or quercetin, 2 mM) was then added (FIGS. 1 and 2).

The results show rapid lipid peroxidation in the control samples of the grilled (oxidized) meat and after an incubation of 180 min the level of the hydroperoxides rose to more than 2000 µM. Addition of antacid attenuated the acidity of the samples to pH 5.0 and further reduced lipid peroxidation (FIG. 1). This attenuation is also associated with the reversed, i.e. oxidative, activity of the catalyst metMb (also see, Kanner et al., ibid).

Figure 2:
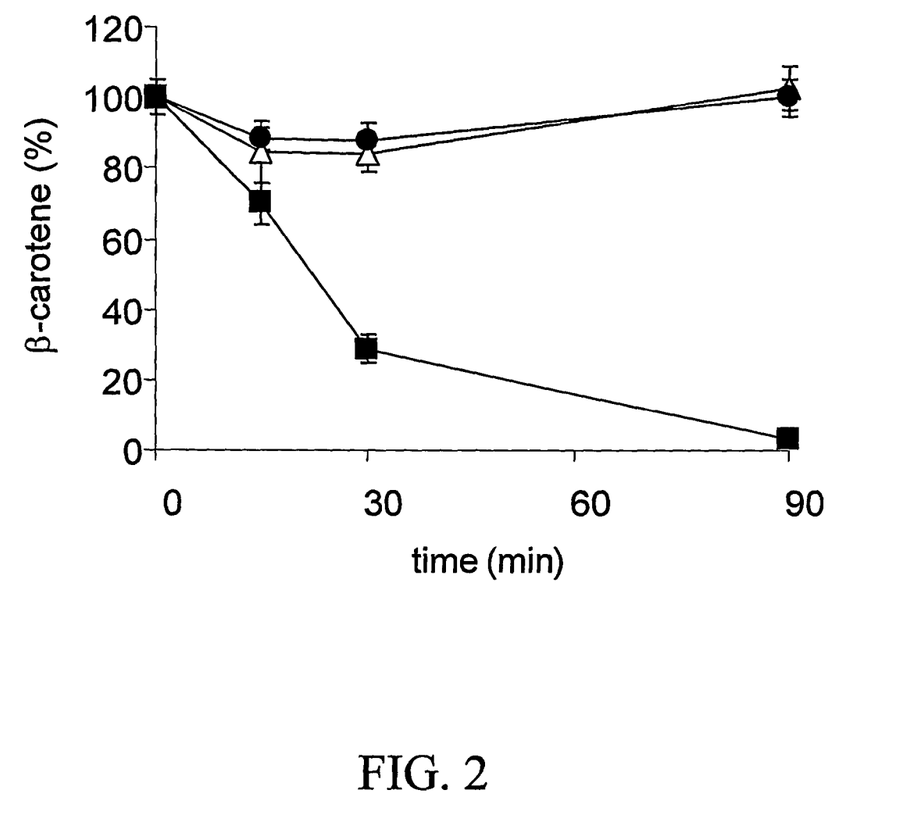
FIG. 2 presents β-carotene co-oxidation in simulated gastric fluid (pH2; triangle) in the presence of $Fe^{3+}$ with catechin (circle) or without catechin (square).

Moreover, in the sample that contained both antacid and catechin not only that lipid peroxidation was inhibited, but the reaction was also reversed and hydroperoxides concentration was reduced to substantially zero (FIGS. 1 and 2).

Example 2

β-Carotene Oxidation

Several studies showed that β-carotene may reduce the risk for prostate cancer. Also, epidemiological studies showed that this molecule is inversely correlated with risk of lung cancer although several intervention studies, among a population of smokers, did not confirm that β-carotene protects against lung cancer.

Recent study (Kanner J, ibid) showed a dramatic increase in β-carotene oxidation under acidic conditions of the gastric simulated fluid. Here B carotene co-oxidation was determined in order to identify free radical damage during lipid peroxidation in the same model system of acid gastric fluid (FIG. 2).

The addition of metmyoglobin to the system catalyzed the bleaching of β-carotene, demonstrating free radical damage to the target molecule. However, the addition of catechin to the same system containing metmyoglobin inhibited β-carotene oxidation by 100% (FIG. 2).

Example 3

Antacid (Zantac®) and Antioxidant Formulation in Babies

GERD may affect up to several million children. Incidence of GERD in infants is reported to be approximately 8% to 10%, and prevalence of reflux esophagitis is reported to be approximately 5%.

Recurrent regurgitation and/or vomiting as well as common GERD reflux symptoms in infants, occur in as many as 50% of newborns (0 to 3 months) and up to 67% of 4-month-old infants. Other symptoms include abdominal discomfort, frequent hiccups, sour burps, bad breath, excessive crying/irritability, feeding refusal/refusal of solid foods.

Untreated GERD may further cause or exacerbate esophagitis, esophageal strictures, dysphagia, chronic cough, apnea, anemia, pneumonia, asthma, failure to thrive ZANTAC® (GlaxoSmithKline) is a histamine $H_2$-receptor antagonist comprising ranitidine which is approved for the treatment of GERD in infants from the age of 1 month.

A baby receives 10 mg/kg/day of Zantac with the addition of an ascorbyl palmitate antioxidant in a dose of 20-50 mg/day. This combined formulation increases the efficiency of Zantac and reduce the overall Zantac dose and length of treatment.

Example 4

Antacid and Antioxidant Formulation in Horses

The stomach of a horse comprises two different parts: squamous epithelium and glandular epithelium wherein a distinct margin, called the margo plicatus, separates these two parts.

Hydrochloric acid (gastric acid) and pepsin are produced in the glandular part which also secretes factors that help to protect the stomach, i.e. a mucus-bicarbonate layer serves to protect the stomach lining both by preventing acid from physical contact with the stomach surface, and by buffering gastric acid at the level of the stomach lining.

This mucous-bicarbonate layer protects only the glandular part of the stomach, and not the squamous part. Other protective factors include prostaglandin E, which causes increased blood flow in the stomach lining, increased secretion of the mucus-bicarbonate layer, and also causes decreases in hydrochloric acid production.

Unlike humans, horses produce gastric acid continually, regardless of whether they are eating regularly. On average the gastric pH is 2.0 or less. The stomach of an un-fed horse is more acidic than usual because acid production cannot be 'turned-off'. The squamous part of the stomach is at great risk at highly acid environment, because it not as protected as the glandular part of the stomach.

Both yearling and adult horses consume pellet forms of food faster than they eat traditional grain diets. The amount of bicarbonate in saliva increases as saliva production increases and so the longer the horse's meal lasts the acidity in the stomach is reduced.

Acid-suppressive therapy in horses may be carried out using drugs that inhibit acid formation. Horses at work respond less favorably to such therapy than hosrse at rest. Acid-suppressive therapy is relatively expensive, however, if the required dose is reduced (e.g. for economic reasons) healing may not occur.

For an antacid to work well in horses it must possess several properties:
(a) easy administration, preferably by adding to the horse's feed;
(b) a small dose must neutralize a large amount of acid and it should coat and protect the mucosa from gastric acid irritation;
(c) the antacids has to be able to adsorb pepsin and other substances that can damage the mucosa;
(d) it should not affect fecal consistency or other harmful side effects.

Kentucky Equine Research has worked to develop an equine antacid that would satisfy the above criteria. Unfortunately, the horses became ataxic and displayed signs of tying-up following high MgO doses (which is one of the common antacids used for humans). Aluminum based antacid raised concern regarding interference with phosphorus absorption, but it appears that aluminum-containing antacids can be safely fed to horses.

Using the composition of the present invention provides the required affect and alleviates ulcer and ulcer-related symptoms efficiently. Exemplary recommended doses are as follows: antacid 20-200 mg per 1 liter of stomach with antioxidant and antioxidant 800 mg per 1 liter of stomach and volume. The antacid is famotidine (20-40 mg/l, omeprazole (20 mg/l) or panteprazole (40 mg/l).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A composition for potentiating antioxidative activities, consisting essentially of:
   (a) at least one classical antacid in a dose capable of neutralizing 100 ml of 0.009 M HCl, such that the composition is capable of elevating the pH in a stomach by at least one pH unit, said elevating the pH being from a pH of 2 to a pH of at least 3;
   (b) at least one antioxidant which is a polyphenol, wherein the relative amount of the at least one antioxidant in the composition is from 30 to 95% w/w of the composition; and, optionally,
   (c) at least one pharmaceutically acceptable carrier,
   said at least one classical antacid being selected from a group consisting of: sodium bicarbonate, potassium hydroxide, aluminum carbonate, aluminum hydroxide, aluminum phosphate, aluminum hydroxy carbonate, dihydroxy aluminum sodium carbonate, aluminum magnesium glycinate, dihydroxy aluminum aminoacetate, dihydroxyaluminum aminoacetic acid, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

2. The composition according to claim 1, wherein the composition is capable of decreasing generation of free radicals and peroxides in the stomach or esophagus more than the same dose of antioxidant in an absence of antacid.

3. The composition according to claim 2, wherein the composition has an ability to decrease at least two fold concentration of free radicals and peroxides in the stomach or esophagus.

4. The composition according to claim 1, comprising at least two distinct antioxidants.

5. The composition according to claim 1, comprising at least two distinct antacids from said at least one classical antacid.

6. The composition according to claim 1, wherein the antioxidant is a polyphenol selected from a group consisting of: anthocyanins; flavonols; flavanols; flavanones; flavanonols; hydrolyzed tannins; proanthocyanidins; lignine; and stilbenes.

7. The composition according to claim 1, wherein the relative amount of the at least one antioxidant in the composition is from 30 to 65% w/w of the composition.

8. The composition according to claim 7, wherein the relative amount of the at least one antioxidant in the composition is from 40 to 60% w/w of the total antacid and antioxidant weight.

9. The composition according to claim 1, wherein the composition is provided in any physical form suitable for oral administration.

10. The composition according to claim 9, the composition having a physical form selected from a group consisting of: tablet, compressed tablet, spheroid, capsule, powder and suspension and liquid.

11. The composition according to claim 10, further comprising at least one ingredient selected from a group consisting of: filler, disintegrant, anticaking agent, film coating, coating solution, binder, stabilizer for solution or for solid forms, entericoating polymer, sweetening agent, glidant, flavor, color, lubricant and plasticizer.

12. The composition according to claim 1, wherein the antioxidant is a polyphenol selected from a group consisting of: chalcones; phenolic acids; anthocyanins; flavonols; flavanols; flavanones; flavanonols; hydrolyzed tannins; proanthocyanidins; phenolamines; lignans; lignine; betalains; stilbenes; cyclic diterpenes; monoterpenes and sesquiterpenes; sesamolin and isoflavones.

13. The composition according to claim 1, wherein said elevating the pH comprises elevating the pH to a pH of up to 9.

14. A composition for potentiating antioxidative activities, consisting essentially of:
  (a) at least one classical antacid in a dose capable of neutralizing 100 ml of 0.009 M HCl, such that the composition is capable of elevating the pH in a stomach by at least one pH unit, said elevating the pH being from a pH of 2 to a pH of at least 3;
  (b) at least one antioxidant which is a polyphenol, wherein the relative amount of the at least one antioxidant in the composition is from 30 to 95% w/w of the composition; and, optionally,
  (c) at least one pharmaceutically acceptable carrier,
  said at least one classical antacid being selected from a group consisting of: sodium bicarbonate, potassium hydroxide, calcium carbonate, calcium phosphate, magnesium carbonate, magnesium glycinate, magnesium hydroxide, magnesium oxide and magnesium trisilicate.

* * * * *